United States Patent [19]

Sawyer et al.

[11] Patent Number: 5,401,653
[45] Date of Patent: Mar. 28, 1995

[54] METHOD FOR CULTURING INSECT CELLS IN A MEDIUM CONTAINING FISH SERUM

[75] Inventors: Evelyn S. Sawyer; Philip J. Sawyer, both of Kennebunkport, Me.

[73] Assignee: Sea Run Holdings, Inc., Kennebunkport, Me.

[21] Appl. No.: 200,639

[22] Filed: Feb. 23, 1994

[51] Int. Cl.$^6$ .............. C12N 5/00; A61K 35/56; A61K 35/60
[52] U.S. Cl. .................. 435/240.2; 435/240.21; 435/240.3; 435/240.31; 424/529; 424/531
[58] Field of Search ............ 435/240.2, 240.21, 240.3, 435/240.31; 424/529, 531

Primary Examiner—Douglas W. Robinson
Assistant Examiner—Jean C. Witz
Attorney, Agent, or Firm—Thomas M. Champagne; Jon L. Roberts

[57] ABSTRACT

A method for culturing insect cells using fish serum. The method uses serum extracted from the blood of fish to culture insect cells for various purposes. The technique has the key advantages of consistent quality, low cross reactivity, safety from infectious agents that would endanger researchers or humans and animals receiving cell culture products as therapy and has appropriate nutrients to maintain the growth of insect cells. Fish serum is used together with designated defined medium to allow insect cells to grow and populations to be maintained. The method may also be used to prevent the attachment of insect cells to cultureware. Serum is derived from the blood of captive stocks of fishes raised under control conditions.

13 Claims, No Drawings

METHOD FOR CULTURING INSECT CELLS IN A MEDIUM CONTAINING FISH SERUM

The present invention relates generally to the culture of cells and more specifically to the culture of insect cells using a serum derived from fish. The technique has significant advantages over the more commonly used technique of using blood serum derived from fetal calves or other mammals as more fully set forth below.

BACKGROUND OF THE INVENTION

Animal cell culture is a basic technique in the fields of biology and medicine. The production of living cells in vitro, in the laboratory, permits numerous applications that would be difficult or impossible in vivo, in the living animal. The culture of animal cells requires a defined medium containing specific quantities of certain chemicals, and in addition for most cells, up to 15% of an undefined nutrient medium usually fetal bovine serum (FBS). Serum from newborn calves and other mammals is also used, but FBS is preferred because of its high level of growth factors and low cross-reactivity with other animal cells. FBS or other mammalian products are also used to coat the surface of culture-ware to promote cell attachment.

The production of FBS in this country is an estimated 700,000 liters annually worth $300 to $400 million. The industry obtains fetal calves for bleeding from slaughter houses, or in some cases, rears herds of cattle for this purpose. These herds are held in as isolated a situation as possible in order to prevent disease. Whole blood is obtained aseptically (by syringe) from an animal, centrifuged to separate cells from serum, and the serum filtered to 0.22 microns to remove most infections agents. Often, serum is heated to 56° C. to inactivate the complement system, a group of immune proteins.

Insect cell culture has also been conducted for many years to develop control methods for this important animal group, and as a model for biological processes in humans and higher animals. More recently, insect cell culture and a virus vector have become a valuable tool for the expression of foreign genes. This technique is superior to the production of foreign proteins by bacteria as higher yields, better "copies" and more complex eukaryotic proteins can be obtained (Smith et al., 1983). Some examples of the recombinant proteins produced by insect cell expression systems are human interferon and interleukin-2, substances that are injected as therapy in human subjects.

An example of the current method of protein production is: 1. culture of an insect cell line (*Spodoptera frugiperda*), 2. insertion of the desired foreign gene in the baculovirus, Autographa Californica Polyhedral Virus (Ac NPV), 3. infection of the insect cell line with this virus, and 4. extraction of the resulting foreign protein from the infected insect cells.

Contamination of cell cultures because of infectious organisms in serum can be a serious problem. Bacteria, fungi, viruses and mycoplasma have been isolated from bovine serum. A decade ago mycoplasma from bovine serum was the second major group of contaminants found in cell culture (Barile, 1977). Now, animal sera are routinely screened for mycoplasma, viruses and other known contaminants. However, a more serious cause for concern is an all-protein infectious agent called a prion for which no test is available (Prusiner, 1982). This prion causes a fatal brain disease in mammals called Bovine Spongiform Encephalopathy (BSE) or "mad cow disease." BSE occurs in sheep, cows, and other mammals, and is most likely the cause of similar neuro-degenerative diseases such as such as Creutzfeld-Jakob disease in humans. In Britain since 1986, mad cow disease has resulted in the destruction of over 100,000 cattle and fears for contamination of the meat supply or other animal products. The disease has also turned up in cattle in many other countries. Consequently, serum from these countries cannot be imported for use in the U.S.

During insect cell culture procedures, most insect cells are maintained in a defined media plus 10% FBS. Therefore any infectious agent in the FBS could contaminate a recombinant protein made by the cells, and could be transmitted to humans receiving this protein as therapy.

The method of the present invention is especially timely as BSE has recently been found in Canadian cattle (Campbell, 1993) and is strongly implicated as the cause of death in Wisconsin mink which were fed protein meal made from dairy cow carcasses (Marsh, 1993). In Europe there is evidence of the disease in humans receiving recombinant human growth hormone contaminated with infected bovine serum (Knauer, 1993).

SUMMARY OF THE INVENTION

It is therefore an object of the present invention to provide a method of extracting a serum from fish that allows the culture of insect cells.

It is yet another objective of the present invention to provide a serum that does not provide any danger from BSE or other pathogens to researchers or to humans and animals receiving medicinal products from insect cell culture.

It is a further object of the present invention to use a serum for cell culture that is free from various mammalian infectious agents that can invalidate the results of scientific testing relating to the culture of insect cells.

It is a further objective of the present invention to create a serum supply of consistent quality for use in cell culture.

It is yet another objective of the present invention to provide a serum for insect cell culture where cells can be prevented from attaching to the cultureware and still remain viable.

It is still a further objective of the present invention to provide a means to enhance the supply of blood serum that is available for research or production in the biotechnology field specifically for the culture of insect cells.

Fish serum offers advantages of safety from mammalian infectious agents and can be used for cell culture applications that now employ bovine or other mammalian sera, and for applications where these sera are ineffective, such as preventing the attachment of insect cells.

The ideal serum for insect cell culture is 1) consistent in quality, 2) has serum immune proteins unlike those of insects for low cross-reactivity 3) is free of infectious agents that would contaminate cell lines, or endanger researchers or humans and animals receiving products made by cell culture and 4) provides the nutrients and growth factors that maintain insect cells and support their growth.

Sera from several species of aquacultured fishes can be used to grow insect cells. Research was conducted with four species of aquacultured fish, representing three families of teleosts; two salmonids, the rainbow trout and its seawater form the steelhead (*Oncorhynchus mykiss*); the Atlantic Salmon (*Salmo salar*); one cyclopterid, the lumpfish (*Cyclopterus lumpus*); and one ictalurid, the channel catfish (*Ictalurus punctatus*). Serum from these fishes is effective and meets the characteristics of the ideal serum including:

Consistent Quality:

Until relatively recently sera from fishes would have been inconsistent in quality, making it inappropriate for cell culture. This is due to the fact that wild stock vary in diet, habitat, genetics, and life history. Now, by using domesticated stocks reared in aquaculture facilities, serum with product consistency similar to serum from land-based cattle herds can be obtained.

Safety:

As previously stated, a major advantage of fish serum for insect cell culture is safety. Serum from fishes is unlikely to contain infectious agents harmful to mammals including humans, fish are cold-blooded animals with body temperatures that approximate the waters where they live. Therefore their pathogens, especially those of cold-water fishes, prefer temperatures well below the body temperatures of most mammals.

Low Cross-reactivity:

Fish serum is unlikely to cause unwanted cross-reactions with insect cells. Fish are an evolutionary distinct group of vertebrates remote from the insects.

Other advantages:

Sera from fishes produced through aquaculture offer additional advantages such as control of environment, genetics, and nutrition of donor animals.

Levels of certain substances in fish serum can be controlled by procedures that would be impossible with mammals for biological or regulatory reasons. For example, mammalian genetic triploids are not viable, but in salmonids, triploids live and grow normally and serum from the female triploid contains no sex steroids (Schreck and Moyle, 1990). Also, fish can be held under conditions unacceptable for mammals, such as total darkness to increase certain hormones such as melatonin in serum.

THE PRESENT INVENTION AND EXPERIMENTAL RESULTS

Using the present invention, the survival and growth of two commonly used line of insect cells in fish serum have been demonstrated. The fish serum used was from two species of salmonids, the rainbow trout and the steelhead (*Oncorhynchus mykiss*), and the Atlantic salmon (*Salmo salar*), the lumpfish (*Cyclopterus lumpus*), and the channel catfish (*Ictalurus punctatus*).

All fishes used as serum sources were progeny of domesticated broodstock and had been inspected for disease according to the American Fisheries Society Blue Book standards. All were sexually immature, in the log-phase of growth, and ranged in size from 1 to 4 kg. Catfish were reared by standard methods on a commercial farm in Alabama, and serum was obtained during routine sampling. All salmonids and lumpfish were reared in Maine. They were fed the same pelleted diet, received the same husbandry, and were held under similar conditions of water flow, oxygen, density, and temperature. Rainbow trout were reared at a freshwater hatchery in Pierce Pond Township, Maine, and the steelhead and salmon were held in seawater net-pens offshore in Eastport, Maine. Lumpfish were reared from the eggs of captive broodstock, and held in the Eastport pens. Water temperatures at the time of bleeding were 8° C. to 12° C. The fish were starved for five days before bleeding to reduce serum levels of proteolytic enzymes, lipids, and non-protein nitrogen (NPN). Each fish was stunned by a blow to the head, immersion in ice-water, or immersion in water containing $CO_2$ or other fish anesthetic, the objective being to stun the fish to a level of loss of reflex reactivity. Whole blood was then drawn by syringe from the dorsal aorta, or in the case of the lumpfish, the caudal vein. Blood was allowed to clot for up to 2 hours, and then centrifuged at $1100 \times g$ for 10 minutes. Serum was removed from the collection tubes, sterilized by passing through a $0.22\mu$ filter, and frozen at $-70°$ C. No heat treatment was used.

Spodoptera cells were used as one example of an insect cell line. They were grown in a flask in Grace's medium supplemented with TC Yeastolate and Lactalbumin Hydrolysate and 5% FBS at 27 C in a closed atmosphere. Cells were removed from the flask by gentle rinsing with the medium. Cells were pelleted, resuspended in serum-free medium, and seeded into 24-well dishes. Sera from four of the fish species (and a control of FBS) was added to the wells to a final concentration of 2% in each well. Cells were sampled at 4, 24, 48, and 96 hours, and those that did not attach were reseeded in new wells in the presence of 10% FBS to determine if they were viable and would now attach with FBS present. Subsamples of cells in the original wells were fixed in 10% formalin at 4 hour periods to determine the number of cells that had attached in the fish sera preparations. After all time points had been assayed, attached cells in the original preparations and those transferred to 10% FBS were stained with crystal violet and survival, growth, and cell adhesion determined.

The method was repeated for Drosophila sp cells using Schjneider's Insect Medium and 10% fish serum.

Results showed that insect cells survived and grew in sera from all species of fishes tested. Insect cells in lumpfish serum survived and did not attach for 48 hours but attached normally when FBS was then added. Compared to the FBS control, insect cells grown in fish serum showed no obvious difference in appearance, and for lumpfish and steelhead serum, cell growth was similar to growth in FBS. Compared to cells in FBS, final cell numbers were lower and attachment less for cells grown in sera from the other fish species tested.

Discussion

The effectiveness of fish serum for growth of insect cells is almost certainly influenced by lipid content, sexual maturity of the donor fish (as reflected in serum steroids), and the growth rate of donor fish.

Serum lipid in the fish species tested was high. Typical triglycerides were greater than 400 mg/dL and cholesterol was greater than 450 mg/dL, ten times or more higher than those of FBS. High serum lipoproteins are potentially growth inhibitory (Ito et al., 1982), therefore we infer that for some insect species lower lipid content in fish serum would improve cell growth.

The best performing sera were from fishes in their maximum growth phase, and beginning (3–4 months before) sexual maturity.

Although only two insect cell line were tested with sera from several species of aquacultured fish, similar results can be expected with other closely related lepidopteran cell lines such as *Mamestra brassicae* or *Bombyx* sp. (Davis et al., 1993). In addition to Drosophila, and Spodoptera other important insect cell lines and sera from other species of fish may be substituted for those disclosed here. particular embodiments is merely illustrative of the principles underlying the inventive concept. Other species of fish and other insect cell lines may be substituted for those disclosed herein. It is therefore contemplated that various modifications of the disclosed embodiments will, without departing from the spirit and scope of the invention, be apparent to persons skilled in the art.

We claim:

1. A method of culturing insect cells comprising culturing the insect cells in culture medium comprising a defined serum free culture medium supplemented with thawed, prepared fish serum, wherein said fish serum is prepared by:
   a. raising fish under controlled conditions such that the diet, habitat, genetics, life history, and reproductive status of the fish remain substantially constant and reproducible;
   b. starving the fish for up to about forty-eight hours;
   c. stunning the fish by non-toxic methods until the fish is unconscious;
   d. withdrawing whole blood from the fish;
   e. allowing the blood to clot;
   f. centrifuging the blood until the blood serum is separated from the blood cells;
   g. removing the serum;
   h. sterilizing the serum; and
   i. freezing the serum.

2. The method of claim 1 wherein said fish is stunned by delivering a sharp blow to the head of the fish.

3. The method of claim 1 wherein said fish is stunned by immersing the fish in water containing carbon dioxide or other fish anesthetic.

4. The method of claim 1 wherein said fish is stunned by immersing the fish in ice water.

5. The method of claim 1 wherein the blood is allowed to clot for up to about two hours.

6. The method of claim 1 wherein the blood is centrifuged at $1100 \times g$ for about ten minutes.

7. The method of claim 1 wherein said fish serum is sterilized by filtering the serum through a 0.22 micron filter.

8. The method of claim 1 wherein said fish serum is frozen to a temperature of $-70$ degrees C.

9. The method of claim 1 wherein the insect cells are grown in 2% fish serum.

10. The method of claim 1 wherein the defined culture medium is selected from the group consisting of Grace's medium and BML TC-10 medium.

11. The method of claim 1 wherein the fish used as a source of blood are selected from the group consisting of *Oncorhynchus mykiss, Salmo salar, Cyclopterus lumpus,* and *Ictalurus punctatus.*

12. The method of claim 1 wherein the insect cells are Spodoptera cells.

13. The method of claim 1 wherein the insect cells are Drosophila cells.

* * * * *